United States Patent
Sarofim et al.

(10) Patent No.: US 8,580,567 B2
(45) Date of Patent: Nov. 12, 2013

(54) METHOD FOR THE AUTOMATED ANALYSIS OF LIQUID SAMPLES USING CENTRIFUGAL FORCE IN A MICROFLUIDIC STRUCTURE

(75) Inventors: Emad Sarofim, Hagendorn (CH); Edwin Oosterbroek, Cham (CH); Claudio Cherubini, Cham (CH); Nenad Milicevic, Allenwinden (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 322 days.

(21) Appl. No.: 12/903,492

(22) Filed: Oct. 13, 2010

(65) Prior Publication Data

US 2011/0250695 A1    Oct. 13, 2011

(30) Foreign Application Priority Data

Oct. 14, 2009   (EP) .................................. 09173065

(51) Int. Cl.
*G01N 21/07*   (2006.01)
(52) U.S. Cl.
USPC ............... 436/45; 422/72; 422/506; 436/165
(58) Field of Classification Search
None
See application file for complete search history.

(56) References Cited

U.S. PATENT DOCUMENTS

| | | | |
|---|---|---|---|
| 6,488,872 B1 | 12/2002 | Beebe et al. | |
| 7,338,760 B2 | 3/2008 | Gong et al. | |
| 2004/0120856 A1 | 6/2004 | Andersson et al. | |
| 2006/0188917 A1 | 8/2006 | Woudenberg et al. | |
| 2008/0003145 A1* | 1/2008 | Nurse et al. ................ | 422/99 |
| 2008/0112855 A1* | 5/2008 | Lee et al. ................ | 422/103 |
| 2008/0206110 A1 | 8/2008 | Andersson et al. | |
| 2008/0237151 A1 | 10/2008 | Cho et al. | |
| 2008/0252905 A1 | 10/2008 | Lee et al. | |
| 2009/0075801 A1 | 3/2009 | Hodko et al. | |
| 2009/0220948 A1* | 9/2009 | Oviso et al. ................ | 435/6 |

FOREIGN PATENT DOCUMENTS

| | | |
|---|---|---|
| EP | 1645882 A1 | 4/2006 |
| EP | 1681553 A2 | 7/2006 |
| EP | 1855038 A2 | 11/2007 |
| EP | 1983347 A2 | 10/2008 |

OTHER PUBLICATIONS

Petrie, Edward M., "Handbook of Adhesives and Sealants", 2nd edition, Chapter 14.10, 441, "Room Temperature Vulcanizing Silicone", 2006.
Schneeberger, Gerald L., "Adhesives in Manufacturing", "RTV Silicone Adhesive Sealants", Chapter 15, pp. 387-405, 1983.

* cited by examiner

*Primary Examiner* — Arlen Soderquist
*Assistant Examiner* — Michelle Adams
(74) *Attorney, Agent, or Firm* — Dinsmore & Shohl LLP

(57) ABSTRACT

A method for the automated analysis of liquid samples using at least one microfluidic structure is disclosed as well as microfluidic structures, a device having at least one of the microfluidic structures, a kit and a system including such microfluidic device. In one embodiment, the method may comprise: transferring a sample into a first fluid reservoir which is in fluid communication with a second fluid reservoir by a flow channel; spinning the microfluidic structure so as to transport the sample into one or more dead-end recesses or chambers; transferring a control fluid into the structure which generates a barrier to flow and diffusion of the sample contained in the one or more dead-end recesses or chambers; and analyzing the sample contained in the one or more dead-end recesses or chambers.

8 Claims, 7 Drawing Sheets

METHOD FOR THE AUTOMATED ANALYSIS OF LIQUID SAMPLES USING CENTRIFUGAL FORCE IN A MICROFLUIDIC STRUCTURE

TECHNICAL FIELD

The embodiments of the present disclosure relate generally to the field of medical diagnostics and in particular, relate to a method, structure, device, kit and system for the automated analysis of liquid samples.

BACKGROUND

Due to an ongoing increase in the number of clinical analyses needed in medical diagnostics, there continues to be a strong demand for the automated analysis of body fluids. In recent years, many efforts have been made to develop new microfluidic devices for the automated centrifugal force based analysis of liquid samples which have minute volumes, e.g. as low as micro-liters, in order to lower sample consumption, hasten analysis times and increase sample throughput.

In the technique of using centrifugal force to drive fluids, the microfluidic device is spun around a spin axis so that samples that are placed at an inner position relative to the spin axis can be transported to an outer position by centrifugal force created as the device rotates. By using centrifugal force for the transport of fluids, sophisticated and expensive mechanical pumps for generating positive or negative pressures acting on the fluids can be avoided.

In general, microfluidic devices for the centrifugal force based analysis of liquid samples include one or more microfluidic structures provided with various functional areas, such as flow channels and reaction chambers. In such microfluidic devices, the reaction chambers typically have greater cross-sectional dimensions than those of the flow channels, and are used for the reaction of samples with one or more reagents to obtain reaction products enabling analysis of substances such as, e.g. nucleic acids, contained therein.

SUMMARY

In one embodiment, a method for the automated analysis of liquid samples involving the use of at least one microfluidic structure is disclosed. The method may comprise transferring the sample into a first fluid reservoir, the first fluid reservoir being in fluid communication with a second fluid reservoir by a flow channel. The method may further comprise spinning the microfluidic structure so as to transport the sample into one or more dead-end recesses by centrifugal force, each of which being in fluid communication with the flow channel by a recess opening. The method may further comprises transferring a control fluid into the first or second fluid reservoirs. The method may further comprise spinning the microfluidic structure to transport the control fluid into the flow channel by a centrifugal force so that control fluid is at least present at the recess opening of the one or more dead-end recesses, the control fluid generating a barrier to flow and diffusion of the sample contained in the one or more dead-end recesses. The method may further comprise analyzing the sample contained in the one or more dead-end recesses.

In another embodiment, a microfluidic structure for the automated analysis of liquid samples, adapted for spinning around a spin axis to generate a centrifugal force, is disclosed. The structure may comprise first and second fluid reservoirs in fluid communication with respect to each other by a flow channel, each of the fluid reservoirs being at an inner position relative to the spin axis, while at least a portion of the flow channel being at an outer position relative to the spin axis. The structure may further comprise one or more dead-end recesses in which a reaction between the sample and one or more reagents takes place, each of which being in fluid communication with the flow channel by at least one recess opening and adapted to be completely filled with the sample by the centrifugal force.

In still another embodiment, a microfluidic device for the automated analysis of liquid samples, adapted for spinning around a spin axis to generate centrifugal force, is disclosed. The microfluidic device may comprise one or more microfluidic structures, each of which may include at least one of: first and second fluid reservoirs communicating with each other by a flow channel, each of the fluid reservoirs being in an inner position as to the spin axis with respect to at least a portion of the flow channel; and one or more dead-end recesses in which a reaction between the sample and one or more reagents takes place, each of which having at least one recess opening in fluid communication with the flow channel and being adapted to be completely filled with the sample contained in the first fluid reservoir by the centrifugal force.

In yet another embodiment, a kit is disclosed and may comprise at least one microfluidic device for the automated analysis of liquid samples adapted for spinning around a spin axis to generate centrifugal force. The microfluidic device in the kit may comprise one or more microfluidic structures, each of which may include, at least one of: first and second fluid reservoirs each of which communicating by a flow channel, each of the fluid reservoirs being in an inner position as to the spin axis with respect to at least a portion of the flow channel; one or more dead-end recesses in which a reaction between the sample and one or more reagents takes place, each of which having at least one recess opening in fluid communication with the flow channel and being adapted to be completely filled with sample by effect of the centrifugal force; and one or more containers, each of which being provided with control fluid, the control fluid being adapted for generating a barrier to flow and diffusion of the sample contained in the one or more dead-end recesses.

In still another embodiment, a system for the automated analysis of liquid samples is disclosed. The system may comprise at least one microfluidic device for the automated analysis of liquid samples being adapted for spinning around a spin axis to generate centrifugal force, the device comprising one or more microfluidic structures, each of which may include at least one of: first and second fluid reservoirs for communicating with respect to each other by a flow channel, each of the fluid reservoirs being in an inner position relative to the spin axis with respect to at least a portion of the flow channel; one or more dead-end recesses in which a reaction between the sample and one or more reagents takes place, each of which having at least one recess opening in fluid communication with the flow channel and being adapted to be completely filled with sample by the centrifugal force; and a centrifuge provided with a rotatable support adapted to support the microfluidic device to co-rotate therewith for spinning the microfluidic device around the spin axis.

These and other features and advantages of the invention will appear more fully from the following description and the accompanying drawings.

BRIEF DESCRIPTION OF THE DRAWINGS

The accompanying drawings, which are incorporated in and constitute a part of the specification, illustrate various embodiments of the invention, and together with the general description given above and the detailed description given below, serve to explain the principles of the invention. In the drawings, similar structures are referred to by like numerals throughout the various embodiments, and in which.

DETAILED DESCRIPTION

Figure 1:
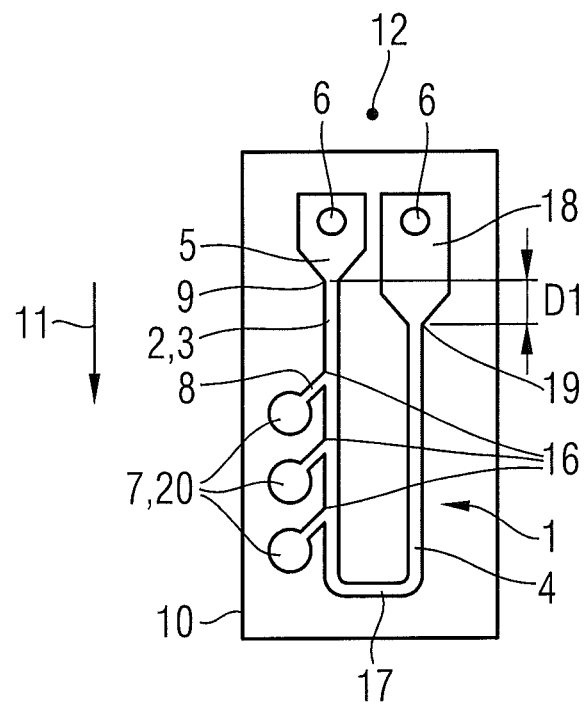
FIG. 1 depicts a schematic top view illustrating an exemplary embodiment of the microfluidic structure of the invention.

When using microfluidic devices, it is often required to isolate samples versus ambient, the ambient versus the samples, or sample aliquots versus another sample aliquots. It is therefore often required to hold a sample or sample aliquot isolated from ambient or from other sample aliquots in functional areas such as, e.g. the reaction chambers. As a matter of fact, samples often need protection against influences of the surroundings or may interfere with other components of the samples and/or reagents, which could adversely affect or even avert sample analysis.

In light of the foregoing, various embodiments of the invention provide an improved method, structure, device, kit and system for the automated analysis of liquid samples.

As used herein, the term "microfluidic" refers to cross-sectional dimensions which typically are on the order of millimeter and sub-millimeter scale. Cross-sectional dimensions may, e.g., range from about 0.01 millimeters to about 2 millimeters. Cross-sectional areas may, e.g., range from about $0.01 \times 0.01$ mm$^2$ to about $2 \times 2$ mm$^2$. Typically, microfluidic features enable manipulation of fluid volumes which, e.g., are on the order of about 100 µl or less at a flow rate, e.g., on the order of about 0.1 to about 100 µl/sec.

As used herein, samples are liquid fluids in which one or more analytes of interest can be present. Samples can include chemical fluids and can be subject to one or more chemical analyses and assays, e.g., drug interaction screening, environmental analysis, identification of organic substances, etc. Samples can also include biological fluids such as body fluids, e.g., blood, serum, urine, milk, saliva, cerebrospinal fluid etc. and can be subject to one or more analyses and assays in medical and pharmaceutical research and clinical diagnosis which may involve in-vitro amplification techniques, e.g., based on the well-known polymerase chain reaction (PCR). Samples can also be pre-processed body fluids such as extracts of body fluids containing target nucleic acids used as starting materials for the PCR. Samples can also include any other fluid of interest as long as automated analysis thereof involves the use of centrifugal force.

As used herein, the term "reagent" indicates any substance, e.g., a solvent or dry-chemical substance which can be mixed with sample to obtain a detectable change in response to one or more analytes contained therein. Reagents can also be mixed with any other reagent(s).

According to one embodiment, a method for the automated analysis of liquid samples is disclosed. The method uses at least one microfluidic structure adapted for spinning around a spin axis to generate centrifugal force. The method includes an act of transferring the liquid sample into a first fluid reservoir of the microfluidic structure which is in fluid communication with a second fluid reservoir by means of a flow channel.

The method may include another act of spinning the microfluidic structure so as to transport the sample into one or more dead-end recesses (reaction-sites or reaction chambers) for a reaction between a sample and one or more reagents to take place. In that, each of the dead-end recesses is in fluid communication with the flow channel by at least one recess opening, that is to say, an opening where the dead-end recess opens into the flow channel.

The method may include another act of transferring another liquid fluid, in the following denoted as "control fluid", into the first or second fluid reservoirs. The control fluid is able to generate a barrier to flow and diffusion of the sample between at least two dead-end recesses or at least one dead-end recess and the ambient.

The method may include another act of spinning the microfluidic structure for transporting the control fluid into the flow channel so that control fluid is at least present at the recess opening of the one or more dead-end recesses.

The method may include another act of analyzing the sample contained in the one or more dead-end recesses.

In the above method, the act of transporting the control fluid into the flow channel may be performed after the sample has already been transported into the one or more dead-end recesses so that the sample is replaced by the control fluid at least in the portions of the flow channel where it communicates with the dead-end recesses. Specifically, e.g., spinning of the microfluidic structure around the spin axis may be performed in a manner to replace the sample contained in the flow channel by the control fluid at least in such areas where flow and diffusion of the sample is to be prevented.

In some embodiments, the above method may comprise an act of providing a microfluidic structure that includes first and second fluid reservoirs which are in fluid communication with respect to each other by a flow channel. Particularly, e.g., each of the fluid reservoirs is at an inner position relative to the spin axis while the complete flow channel or at least a portion thereof is at an outer position relative to the spin axis, that is to say, has a larger distance from the spin axis than each of the first and second fluid reservoirs. The microfluidic structure further may include one or more dead-end recesses for a reaction between the sample and one or more reagents to take place. Each of the dead-end recesses may be in fluid communication with the flow channel by at least one recess opening and may be formed in such a manner that it can be completely filled with the sample received from the first fluid reservoir by effect of centrifugal force.

In some embodiments, the one or more dead-end recesses can be provided with one or more, e.g. dry-chemical, reagents for reacting with samples received therein. Specifically, e.g., plural dead-end recesses may contain one or more reagents which are similar or different with respect to each other.

In some embodiments, the method enables the distribution of one sample to many dead-end recesses in order to enable parallel analysis of one sample.

In some embodiments, analysis of one sample in plural dead-end recesses may be based on one analytical method involving the use of one or more similar reagents in the dead-end recesses.

In some embodiments, analysis of one sample in plural dead-end recesses may be based on various analytical methods varying among the dead-end recesses involving the use of one or more different reagents.

As described above, in some embodiments the control fluid can generate a barrier to flow and diffusion of sample contained in the one or more dead-end recesses. The control fluid isolates the dead-end recesses with respect to fluid flow and diffusion so that sample contained in individual dead-end recesses is isolated against external influences and vice versa. In that, the control fluid isolates the dead-end recesses with respect to each other and the ambient.

In some embodiments, the control fluid may be essentially non-miscible with the sample, that is to say, is chosen to stay mainly unmixed with the sample (and vice versa) at typical parameters for filling of the sample and the control fluid into the microfluidic structure.

In some embodiments, the control fluid may be mainly insoluble in the sample (and vice versa), which, e.g., may be reached by the specific design of the sample and control fluid such as choosing one to be hydrophilic and the other one to be hydrophobic. It may be preferable that solubility of control fluid in the sample (and vice versa) is less than about 1%.

In some embodiments, the control fluid is designed to reduce or even inhibit mass transport between dead-end recesses and/or between dead-end recesses and the ambient. Specifically, e.g., mass transport based on water diffusion and/or analyte diffusion and/or reagent diffusion can disturb an analysis of the sample or make it even impossible.

In some embodiments, the control fluid may be chosen to essentially not influence the sample or to essentially not influence the analytical reaction performed with the sample in the non-solidified and solidified state.

In some embodiments, the density of the control fluid may be chosen to be smaller than the density of the sample in order to avoid the control fluid to flow into the dead-end recesses during centrifugal transport of the control fluid.

In some embodiments, the control fluid may be adapted to generate a barrier to flow and diffusion between at least two dead-end recesses or at least one dead-end recess and the ambient, when present in at least a portion of the flow channel connecting the dead-end recesses.

In some embodiments, the control fluid solidifies after being filled (transported) into the flow channel. Solidification of the control fluid may, e.g. be based on a liquid-solid transition, a viscous-thixotrop transition, a sol-gel transition or the like.

In some embodiments, the control fluid may be solidified by contacting the sample. In some embodiments, in order to avoid a too early generation of the barrier during the centrifugal force driven transport of the control fluid into the flow channel, solidification of the control fluid may be required to be sufficiently slow so as to allow the control fluid to be transported within the flow channel.

In some embodiments, the control fluid can form a barrier to flow and diffusion within a time interval in a range of from one or a few minutes to less than 30 minutes.

In some embodiments, solidification of the control fluid may be based on polymerization. Polymerization of the control fluid, e.g., may be initiated by water or any other suitable triggering fluid contained in the sample. In some embodiments, the water contained in the sample initiates the polymerization of the control fluid.

In some embodiments, solidification of the control fluid may be based on reactions different from the polymerization such as, e.g., hydrolysis.

In some embodiments, prior to solidification, the control fluid has a viscosity in a range of from about 5 to about 5000 mPa·sec. In some embodiments, the control fluid has a viscosity in a range of from about 50 to about 500 mPa·sec.

In some embodiments, a contact angle between the control fluid and the microfluidic structure may be smaller than about 90°. In still other embodiments, the contact angle between the control fluid and the microfluidic structure may be smaller than about 50°.

In some embodiments, after solidification, the control fluid has a shore-hardness in a range of from about 0 A to about 100 A. Instill other embodiments, the control fluid has a shore-hardness in a range of from about 10 A to about 60 A.

In some embodiments, the control fluid may be chosen to be sufficiently resistant to higher temperatures. Specifically, in the case of thermo-cycling nucleic acids, e.g., for performing the polymerase chain reaction, the control fluid is resistant to temperatures of more than about 120° C.

In some embodiments, the control fluid may be chosen to exhibit sufficient adherence to the microfluidic structure and sufficiently low permeability to water vapor in the solidified state.

In some embodiments, the control fluid may be embodied as one of those substances known as "Room Temperature Vulcanisates (RTVs)" which are, e.g., described in detail in the "Handbook of Adhesive and Sealants", Edward M. Petri, 2nd edition, chapter 14.1, 44.1, "Room Temperature Vulcanizing Silicone" and "Adhesives in Manufacturing", Gerald L. Schneeberger, Chapter 15, "RTV Silicone Adhesive Sealants".

In some embodiments, especially in the case of water-triggered polymerization of RTV-silicones, the control fluid may be a cross-linker which forms, e.g., acetone or alcohol as a by-product.

In some embodiments, control fluids may be used of which the reaction products are organo-siloxanes (i.e. silicones) according to the following formula:

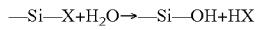

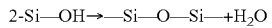

In some embodiments, the control fluid may be based on one or more cross-linking substances selected from the group consisting of polyacrylates, polymethacrylates, polyester, polyurethane and epoxides.

In some embodiments, in which solidification of the control fluid is obtained by polymerization which does not require water as the triggering substance, such a control fluid may contain other catalysts which are already present in the control fluid when it is loaded into the microfluidic structure. The control fluid, e.g., may be polymerized upon elapse of a specified time interval and/or when heated to a specified temperature. The control fluid may be provided in a kit ready to use or, alternatively, to be pre-mixed prior to use.

In some embodiments, the control fluid undergoes no major change after filling into the microfluidic structure. A suitable control fluid for water-based samples may be, e.g., a paraffin oil.

In some embodiments, the control fluid may be thixotropic in nature.

In some embodiments, the dead-end recesses (reaction chambers) may be provided (pre-filled) with one or more reagents, e.g., a dry-chemical reagent, prior to being filled with the sample. Filling the dead-end recesses with a sample thus enables a reaction between the sample and the one or more reagents to take place to thereby obtain a reaction product going along with a detectable change, e.g. an optically detected change, of the sample.

In some embodiments, the method may include reacting the sample with site-specific reagent(s) present in the dead-end recesses. In some embodiments, the method may further include confining the sample or the reaction products obtained in the one or more dead end recesses by forming a barrier to flow and diffusion by using the control fluid. In some embodiments, the method may further include analyzing the sample or the reaction products confined by the control fluid in the one or more dead end recesses. In some embodiments, the sample or the reaction products are confined by the control fluid in the one or more dead end recesses by solidifying the control fluid.

In some embodiments, instead of pre-filling the dead-end recesses with one or more reagents, a liquid sample and one or more reagents for reacting with the sample are transferred into the one or more dead-end recesses by centrifugal force. Specifically, e.g., sample and one or more reagents can be transferred into the first fluid reservoir to obtain a sample-reagent mixture, followed by trans-porting the sample-reagent mixture into the dead-end recesses by the effect of a centrifugal force. Alternatively, sample and one or more reagents can be pre-mixed prior to transfer to the first fluid reservoir to obtain a sample-reagent mixture which then is transferred to the first fluid reservoir.

In some embodiments, the method may comprise an act of having the control fluid solidified in at least a contact area of the sample and the control fluid.

In some embodiments, the method may comprise an act of initiating solidification of the control fluid by an initiating substance, e.g. water, contained in the sample. In some embodiments, solidification of the control fluid is initiated by water contained in the sample. The reasons for this are:

good stability of the control fluid during storage (without humidity);
no pre-mixing of the control fluid prior to its transfer to the microfluidic structure;
solidification of the control fluid may be initiated at temperatures as low as less than 50° C., which often proves advantageous for the specific assay used;
control fluid can be chosen to be low-viscous; and
solidification starts with contacting the sample.

Basically, in PCR the samples are repeatedly put through a sequence of amplification steps which includes melting the nucleic acids to obtain denatured single polynucleotide strands, annealing short primers to the strands, and extending the primers to synthesize new polynucleotide strands along the denatured strands to make new copies of double-stranded nucleic acids. The amplification of nucleic acids by PCR thus requires the samples to be cycled through a series of temperature excursions in which predetermined temperatures are kept constant for specific time intervals. Specifically, the temperature of the samples usually is raised to around 90° C. for denaturing the nucleic acids and lowered to 40° C. to 70° C. for annealing and primer extension along the polynucleotide strands.

In some embodiments, the method may comprise an act of (thermo-)cycling the sample contained in the one or more dead-end recesses through a series of temperature excursions in which predetermined temperatures are kept constant for specific time intervals to enable the polymerase chain reaction. In order to optically detect the amplified nucleic acids, e.g., fluorescence related to the concentration thereof can be measured.

In some embodiments, the method may comprise an act of analyzing the sample contained in one or more dead-end recesses of one microfluidic structure using an analytical method.

In some embodiments, the method may comprise an act of analyzing the sample contained in plural dead-end recesses of the microfluidic structure using plural analytical methods which are different with respect to each other.

In some embodiments, the method may comprises an act of analyzing the sample contained in one or more dead-end recesses of plural microfluidic structures using one analytical method.

In some embodiments, the method may comprise an act of analyzing the sample contained in one or more dead-end recesses of plural microfluidic structures using plural analytical methods which are different with respect to each other.

In some embodiments, the method may comprise an act of analyzing plural samples contained in one or more dead-end recesses of plural microfluidic structures using one analytical method.

In some embodiments, the method may comprise an act of analyzing plural samples contained in one or more dead-end recesses of plural microfluidic structures using plural analytical methods which are different with respect to each other.

In some embodiments, the method may comprise an act of analyzing one or more samples contained in one or more dead-end recesses of plural microfluidic structures in parallel using one or plural analytical methods which are different with respect to each other.

According to another embodiment, use of the above-described method embodiments for the automated in-vitro amplification of nucleic acids by means of the polymerase chain reaction (PCR) or by any other nucleic acid amplification technique such as isothermal amplification reaction is disclosed.

According to a yet another embodiment, a microfluidic structure for the automated analysis of liquid samples is disclosed.

Embodiments of the microfluidic structure, e.g., may be used in chemistry, bio-chemistry and medicine including in-vitro diagnostics usually involving mixing between samples and reagents to obtain reaction products as well as detecting the result of such reactions. Such embodiments, e.g., may be used for diagnostic assays such as clinical chemistry assays and immunoassays. In some embodiments, the microfluidic structure may be dedicated to perform a set of various analytical methods or assays of one sample. Typical diagnostic assays include qualitative and/or quantitative analysis of analytes contained in the sample such as nucleic acids. The microfluidic structure in particular, e.g., may be used for in-vitro amplification techniques adapted for the amplification of nucleic acids, e.g., based on the polymerase chain reaction (PCR). A set of analytical methods may, e.g., include gene expressions analysis and genetic testing as genotyping of virus or bacteria.

The microfluidic structure in some embodiments may be adapted for spinning around a spin axis to generate centrifugal force as the microfluidic structure rotates. The microfluidic structure may include a first fluid reservoir and a second fluid reservoir which are in fluid communication with respect to each other by means of a flow channel. Each of the fluid reservoirs may be at a (radial-)inner position with respect to the spin axis while the flow channel or at least a portion thereof may be at a (radial-)outer position with respect to the spin axis. The microfluidic structure in some embodiments may further include one or more dead-end recesses or troughs (cells or cavities) for a reaction between the sample and one or more reagents to take place. Each of the dead-end recesses may be in fluid communication with the flow channel by at least one recess opening and may be formed in such a manner to be completely (gas-free) filled with sample received from the first fluid reservoir by effect of centrifugal force. Hence, in some embodiments, the flow channel communicates with one or more dead-end recesses arranged in a manner to receive fluids, such as the sample, and to be completely filled by the effect of a centrifugal force. In such embodiments, this gas-free filling of the dead-end recesses is reached by the fact that each of the dead-end recesses is free from undercut portions with respect to the centrifugal force.

In some embodiments, in order to avoid undercut portions, the flow channel of the microfluidic structure may be in fluid communication with the one or ore dead-end recesses in a (radial-)innermost portion thereof relative to the spin axis.

In some embodiments, the first fluid reservoir opens into a first channel portion of the flow channel and the second fluid reservoir opens into a second channel portion of the flow channel, wherein the first and second channel portions are being fluidically connected by a third channel portion. Specifically, e.g., each of the first and second channel portions (as seen from the fluid reservoir) extends in such a direction that it is in parallel alignment to the centrifugal force or at least has a directional component in parallel alignment to the centrifugal force while the third channel portion extends in such a direction that it is in orthogonal alignment to the centrifugal force or at least has a directional component in orthogonal alignment to the centrifugal force. More specifically, e.g., the flow channel may include, but is not limited to, one first and one second channel portion and one third channel portion connecting the first and second channel portions at their outer end sections relative to the spin axis, wherein each of the first and second channel portions at least approximately extends along the direction of the centrifugal force generated as the microfluidic rotates while the third channel portion is in orthogonal alignment thereto. For example, the flow channel, e.g., may be provided U-shaped.

In some embodiments, one of the first and second channel portions of the flow channel may be in fluid communication with one or more dead-end recesses.

In some embodiments, both of the first and second channel portions are in fluid communication with one or more dead-end recesses.

In some embodiments, reservoir openings where the first and second fluid reservoirs open into the flow channel are distanced with respect to each other relative to the centrifugal force.

In some embodiments, reservoir openings where the first and second fluid reservoirs open into the flow channel are not distanced with respect to each other relative to the centrifugal force.

In some embodiments, the one or more dead-end recesses are being provided with one or more reagents, e.g. dry-chemical reagents, for a reaction with the samples received therein.

In some embodiments, plural dead-end recesses contain one or more reagents which are similar with respect to each other.

In some embodiments, plural dead-end recesses contain one or more reagents which are different with respect to each other.

In some embodiments, the flow channel may be in fluid communication with one or more dead-end recesses by intermediate channels which, being part of the dead-end recesses, branch-off from the flow channel. Specifically, e.g., individual dead-end recesses may be comprised of a cavity fluidically connected to the flow channel by the intermediate channel.

In some embodiments, cross-sectional dimensions of the cavities may be greater than cross-sectional dimensions of both the flow channel and intermediate channels. In other words, each of the intermediate channels may have a cross-sectional dimension smaller than the cavity fluidically connected therewith so that the samples may be readily kept in the cavities of the dead-end recesses.

In some embodiments, each of the first and second fluid reservoirs may be provided with at least one port for transferring/removing fluid to/from the fluid reservoir.

According to a yet another embodiment, a microfluidic device for the automated analysis of liquid samples is disclosed.

In some embodiments, the microfluidic device can have a disk-like shape and can be fixed to a rotatable supporting device or platform which, e.g., can be provided by a centrifuge to co-rotate therewith.

In some embodiments, the microfluidic device may be removably fixed to the rotatable supporting device enabling the microfluidic device to be readily mounted to the supporting device or removed therefrom after sample analysis. The rotatable supporting device, e.g., may be driven by means of an actuator such as, e.g., an electric motor.

In some embodiments, the microfluidic device may be made of plastic material, e.g., based on organic polymers such as polymethylmethacrylate (PMMA), polycarbonate (PC), polyethylene (PE) or polypropylene (PP).

In some embodiments, the microfluidic device may be a disposable element which, e.g., may be intended for single use only.

In some embodiments, the microfluidic device may be an assembly of several parts which, e.g., may be structured by one or more techniques selected from the group consisting of polymer injection, thermoforming, hot-embossing and deep drawing. Specifically, flat members of the assembly, e.g., may be punched or cut. For flat members, laminated or various polymers and metals, e.g., may be used. For the assembly of plural parts, various methods may be used such as laser welding, thermal sealing, ultrasound welding, laminating or gluing.

In some embodiments, the microfluidic device may include one microfluidic structure according to any one of the embodiments described herein.

In some embodiments, the microfluidic device may includes a plurality of the microfluidic structures described herein and which in some embodiments, e.g., may be circumferentially arranged with respect to each other to be spun around the spin axis.

In some embodiments, the microfluidic device includes a plurality of the microfluidic structures as described herein which are dedicated to one analytical method. Specifically, the dead-end recesses of the microfluidic structures, e.g., may be provided with one reagent.

In some embodiments, the microfluidic device includes a plurality of the microfluidic structures as described herein which are dedicated to a plurality of analytical methods at least some of which are different with respect to each other. Specifically, the dead-end recesses of the microfluidic structures dedicated to different analytical methods, e.g., may be provided with one or more different reagents.

In some embodiments, the microfluidic device includes a plurality of the microfluidic structures as described herein wherein one first fluid reservoir and one second fluid reservoir are in fluid communication with plural flow channels.

In some embodiments, the microfluidic device includes a hub for connection to a centrifuge for spinning the device around the spin axis for generating centrifugal force as the device rotates.

According to a yet another embodiment, a kit for the automated analysis of liquid samples is disclosed. The kit includes at least one microfluidic device as described herein and one or more containers, each of which being provided with control fluid. As described above, the control fluid may be adapted for generating a barrier to flow and diffusion of the sample contained in the one or more dead-end recesses.

In some embodiments, the kit further comprises one or more containers, each of which being provided with one or more reagents, e.g., adapted to perform the polymerase chain reaction of nucleic acids contained in the sample.

According to a yet another embodiment, a system for the automated analysis of liquid samples is disclosed. The system includes one or more microfluidic devices as described herein and a centrifuge provided with a rotatable support adapted to support the microfluidic device to co-rotate therewith for spinning the microfluidic device around the spin axis.

In some embodiments, the system may further include an analyzer adapted for analyzing the sample contained in the one or more dead-end recesses. The analyzer may, e.g., include a detection arrangement to optically detect reaction products contained in the dead-end recesses based on optical signals propagating between reaction products and the detection arrangement.

In some embodiments, the detection arrangement may include one or more detectors to optically detect reaction products such as, but not limited to, charge coupled devices (CCDs), diode arrays, photomultiplier tube arrays, charge injection devices (CIDs), CMOS detectors and avalanche diodes.

In some embodiments, the detection arrangement may also include one or more excitation lamps to excite emission of fluorescence light by the reaction products.

In some embodiments, the detection arrangement may further include light guiding elements such as, but not limited to, lenses and mirrors and/or light separating elements such as, but not limited to, transmission gratings, reflective gratings and prisms.

In some embodiments, the dead-end recesses of the microfluidic structure(s) are enclosed by one or more optically transparent covers such as a transparent foil or lid in order to avoid evaporation of the reaction mixtures contained therein and to shield them from external influences. Particularly, e.g., the transparent cover allows for an optical detection of the reaction products even during progress of the reaction. In that, the transparent cover may allow radiation such as excitation light to be transmitted to the reaction products and emitted fluorescent light from the reaction products to be transmitted back to the one or more detectors, e.g., during thermal cycling of the samples.

The system may be used for the automated analysis of liquid samples and may further be adapted for post-analysis tasks and the generation of analytical results. Basically, the system may include one or more of the following components: a sample storage, a control liquid storage, a reagent storage, incubators, mixers, a device storage, a liquid and solid waste, an automotive liquid handler for transferring liquids, a transfer means for transporting samples and reagents, an analyzer, a real-time fluorescence thermal cycler, a process controller, a process surveillance means, an user interface, a data storage and data communication interface. Specifically, the process controller can be set up to control the method for the automated analysis of liquid samples as-above described.

According to a yet another embodiment, use of the above-described system for the automated in-vitro amplification of nucleic acids, e.g., by means of the polymerase chain reaction (PCR) is disclosed.

The various embodiments of the present invention will now be described according to a number of illustrated embodiments set forth in detail below with reference to the accompanying drawings. With particular reference to FIG. 1, an exemplary embodiment of a microfluidic structure 1 for the automated analysis of liquid samples such as body fluids is explained. The microfluidic structure 1 can be spun around a spin axis 12 to generate centrifugal force as the microfluidic structure 1 rotates. The direction of the centrifugal force is indicated by arrow 11. For that purpose, the microfluidic structure 1 can be fixed to a rotatable supporting device or platform (not illustrated) in a manner to co-rotate therewith. The microfluidic structure 1 may be removably fixed to the supporting device to be readily mounted to or removed therefrom after analysis.

The microfluidic structure 1 may include a solid body 10, e.g., made of plastic material which, e.g., may have a disk-like or rectangular shape. The microfluidic structure 1, e.g., may be intended for single use only to be disposed after one sample analysis. While only one microfluidic structure 1 is shown in FIG. 1 for the purpose of illustration only, it is to be understood that more than one microfluidic structure 1 may be envisaged according to the specific demands of the user. Particularly, a plurality of microfluidic structures 1, e.g., may be arranged side by side or can be circumferentially arranged with respect to each other relative to the rotational movement of the microfluidic structure 1. The microfluidic structure 1 may be produced by any conventional molding technique.

Specifically, e.g., the structure 1 may include a (main) flow channel 2 which being in U-shape is comprised of one linearly extending first channel portion 3 and one linearly extending second channel portion 4 connected by one third channel portion 17 at their outer end sections. While each of the first and second channel portions 3, 4 mainly, but not necessarily, may extend along the direction of centrifugal force 11 generated as the structure 1 rotates, the third channel portion 17 mainly, but not necessarily, extends in a direction orthogonal to the centrifugal force 11.

The microfluidic structure 1 may further include a first fluid reservoir 5 and a second fluid reservoir 18 adapted to receive fluids which are in fluid communication by the flow channel 2. Each of the fluid reservoirs 5, 18 may have a larger cross-sectional dimension than the flow channel 2 communicating therewith. Furthermore, each of the fluid reservoirs 5, 18 may be provided with a port 6 for transferring/removing any fluid of interest into/from the fluid reservoir 5, 18.

As illustrated in the figures, the first fluid reservoir 5 opens into the first channel portion 3 at first reservoir opening 9, while the second fluid reservoir 18 opens into the second channel portion 4 at second reservoir opening 19. Specifically, e.g., the first and second reservoir openings 9, 19 may have a non-zero distance D1 with respect to each other relative to the direction of the centrifugal force 11. Accordingly, one reservoir opening (e.g. the right one) may have an inner position relative to the spin axis 12 while the other reservoir opening (e.g., the left one) may have an outer position relative to the spin axis 12.

With continued reference to FIG. 1, the first channel portion 3 may be in fluid communication with plural dead-end recesses (reaction-sites or reaction chambers) in which a reaction between a sample and one or more reagents can take place. For purposes of discussion hereinafter, the dead-end recesses are embodied and depicted as reaction chambers 7. Although three reaction chambers 7 are shown, such a number is only for the purpose of illustration and those of skill in the art will appreciate that any other number of reaction chambers 7 may be envisaged according to the specific demands of the user.

Specifically, e.g., each of the reaction chambers 7 may be comprised of a trough or cavity 20 connected to one linearly extending intermediate channel 8 that fluidically communicates with the flow channel 2 by a recess or chamber opening 16. Each of the cavities 20 may have a cross-sectional dimension larger than that of the flow channel 2. Otherwise, each of the intermediate channels 8 may have a cross-sectional dimension smaller than that of the cavity 20 connected therewith.

The reaction chambers 7 are formed in a manner that they can be completely filled with fluid by the centrifugal force 11. Specifically, e.g., each of the reaction chambers 7 may be free from undercut portions relative to the direction of the centrifugal force 11. More specifically, e.g., each intermediate channel 8 branches-off from the flow channel 2 towards the cavity 20 in a direction which includes a directional component parallel to the centrifugal force 11. In other words, each intermediate channel 8 may be inclined relative to the centrifugal force 11 by an angle of less than about 90°. Hence, the chamber opening 16 of each reaction chambers 7 may be the innermost part of the reaction chamber 7 relative to the spin axis 12.

In the microfluidic structure 1, each of the cavities 20 may, e.g., contain one or more dry-chemical reagents for reacting with the sample to obtain a detectable change which can be detected by an analytical method. For multiplex analysis of a sample, at least two cavities 20 may contain two different reagents in order to execute two different reactions. In some embodiments, the dry-chemical reagent can dissolve in the sample upon entry of the sample into the cavities or during execution of the analysis, e.g., triggered upon thermal treatment.

The cross-sectional dimensions of the microfluidic features of the microfluidic structure 1 may, e.g., range from about 0.01 millimeters to about 2 millimeters. Also, cross-sectional areas may, e.g., range from about $0.01 \times 0.01$ mm$^2$ to about $2 \times 2$ mm$^2$.

With particular reference to FIGS. 2A to 2E, an exemplary embodiment of a method for the automated analysis of liquid samples using the microfluidic structure 1 of FIG. 1 is explained.

Figure 2A:
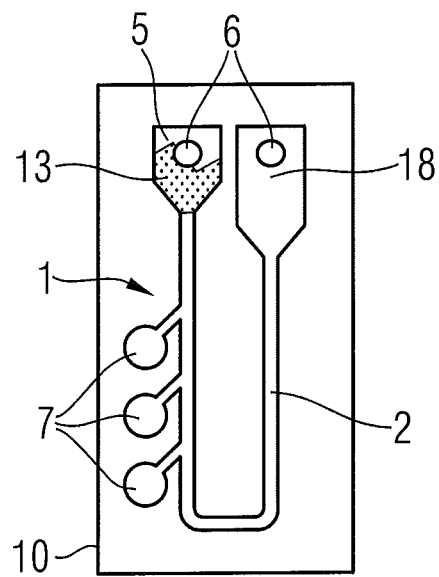
FIGS. 2A-2E depict schematic top views illustrating an exemplary embodiment of the method for the automated analysis of liquid samples using the microfluidic structure of FIG. 1.

Accordingly, in a first step of action, a liquid sample 13 such as a body fluid is introduced via the port 6 of the first fluid reservoir 5 which can be performed by an automatic pipetting operation, e.g., using a pipetting robot (FIG. 2A).

Figure 2B:
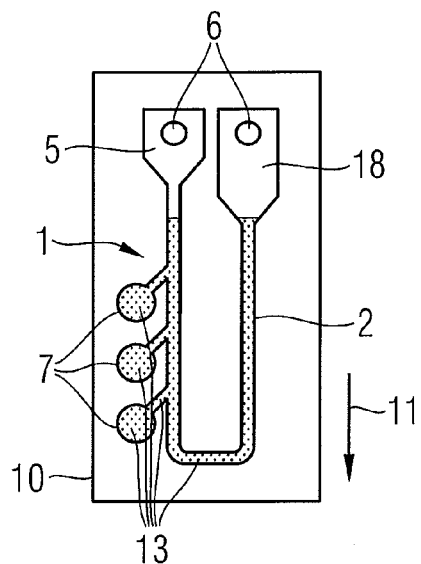

Then, in a second step of action, the microfluidic structure 1 is spun around the spin axis 12 to generate centrifugal force 11 for transporting the liquid sample 13 into the flow channel 2 and the reaction chambers 7. Driven by the centrifugal force 11, the liquid sample 13 is moved to the second reservoir opening 19 of the second fluid reservoir 18 (FIG. 2B).

Figure 2C:
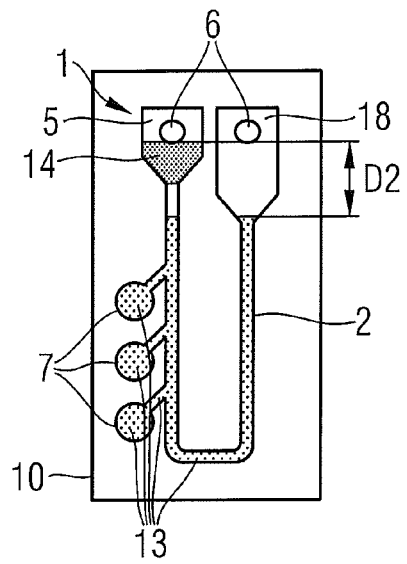

After that, in a third step of action, a control fluid 14 is introduced via the same port 6 (e.g. the left one) as used for introducing the liquid sample 13 into the first fluid reservoir 5 by an automatic pipetting operation, e.g., using a pipetting robot. Due to the non-zero distance (D1, see FIG. 1) between the first and second reservoir openings 9, 19, upper levels of the control fluid 14 contained in the first fluid reservoir 5 and the liquid sample 13 contained in the flow channel 2 have a non-zero distance (D2) with respect to each other. Otherwise, a small air gap is present between the control fluid 14 contained in the first fluid reservoir 5 and the liquid sample 13 contained in the flow channel 2 (FIG. 2C).

Figure 2D:
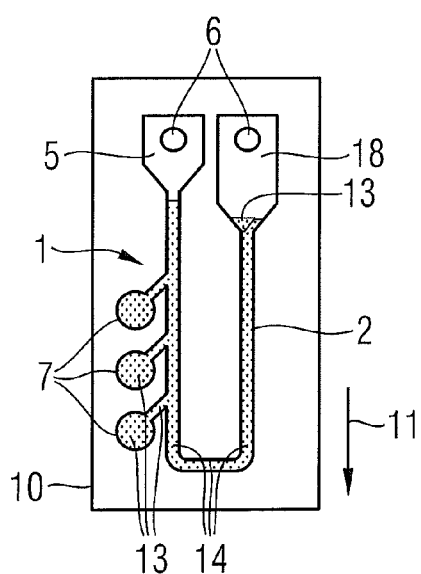

Then, in a fourth step of action, the microfluidic structure 1 is spun around the spin axis 12 to create centrifugal force 11 to drive the control fluid 14 into the flow channel 2 to thereby replace the liquid sample 13 in the flow channel 2 and to enable contact between the control fluid 14 and the sample 13 contained in the reaction chambers 7 at chamber openings 16 (FIG. 2D).

Figure 2E:
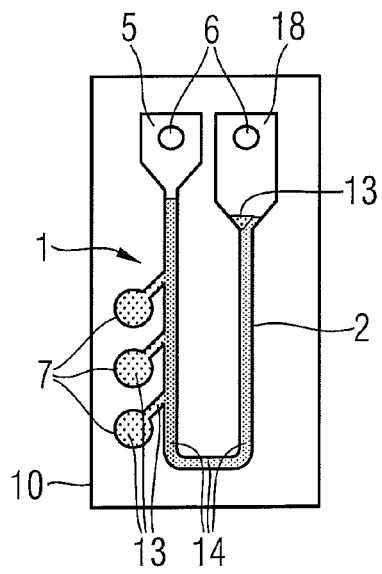

The control fluid 14 then is allowed to solidify initiated by contact between the control fluid 14 and the liquid sample 13 contained in the reaction chambers 7 so as to form a barrier to flow and diffusion for the liquid sample 13 contained in the reaction chambers 7. Specifically, e.g., the solidified control fluid 14 is a barrier to flow and diffusion between the plural reaction chambers 7 and between the reaction chambers 7 and the ambient. The control fluid 14, e.g., in some embodiments may be based on silicone so that solidification of the control fluid 14 can be triggered by water contained in the liquid samples 13 (FIG. 2E).

In the above method, as described in connection with FIGS. 2A to 2E, the control fluid 14 is chosen in one embodiment to be substantially non-miscible with liquid sample 13 in order to enable replacement of the liquid sample 13 in the flow channel 2 by the control fluid 14. In such embodiment, the control fluid 14 is further able to generate a barrier to flow and diffusion in the case of contacting the liquid sample 13, wherein solidification of the control fluid 14 is initiated by water contained in the liquid sample 13. In some embodiments, the control fluid 14 is selected such that the reaction product of which is an organo-siloxane (silicone). In still other embodiments, the control fluid 14 is sufficiently solidified so as to form a barrier to flow and diffusion for the sample 13 contained in the reaction chambers 7 within a time interval of a few minutes.

Having the sample 13 isolated in the reaction chambers 7 by the solidified control fluid 14, the sample can react with one or more reagents contained therein to obtain a reaction product which, e.g., can be optically detected. For example, the sample 13 being isolated in the reaction chambers 7 can be repeatedly put through a sequence of temperature excursions in which predetermined temperatures are kept constant for specific time intervals to enable the PCR.

While not shown in the figures, the method also includes a further act of analyzing the liquid sample 13 contained in the reaction chambers 7 by means of an analyzer to optically detect a reaction product of the sample 13. The method, e.g., may be used for the in-vitro amplification of nucleic acids, e.g., by means of the polymerase chain reaction (PCR). The method may, e.g., include a further act of detecting the amplified nucleic acids. The analyzer includes a detection arrangement (not illustrated) to optically detect reaction products contained in the reaction chambers 7. The detection arrangement may include one or more excitation lamps to excite emission of fluorescence light by the reaction products and may also include one or more detectors to optically detect fluorescence light, e.g., indicating concentration of amplified nucleic acids.

In the above method as-described in connection with FIGS. 2A-2E, instead of pre-filling the reaction chambers 7 with one or more reagents or additionally thereto, a sample-reagent mixture containing liquid sample 13 and one or more reagents for reacting with the sample 13 can be transferred to the first fluid reservoir 5, followed by transporting the sample-reagent mixture into the flow channel 2 and reaction chambers 7 by effect of centrifugal force.

Figure 3:
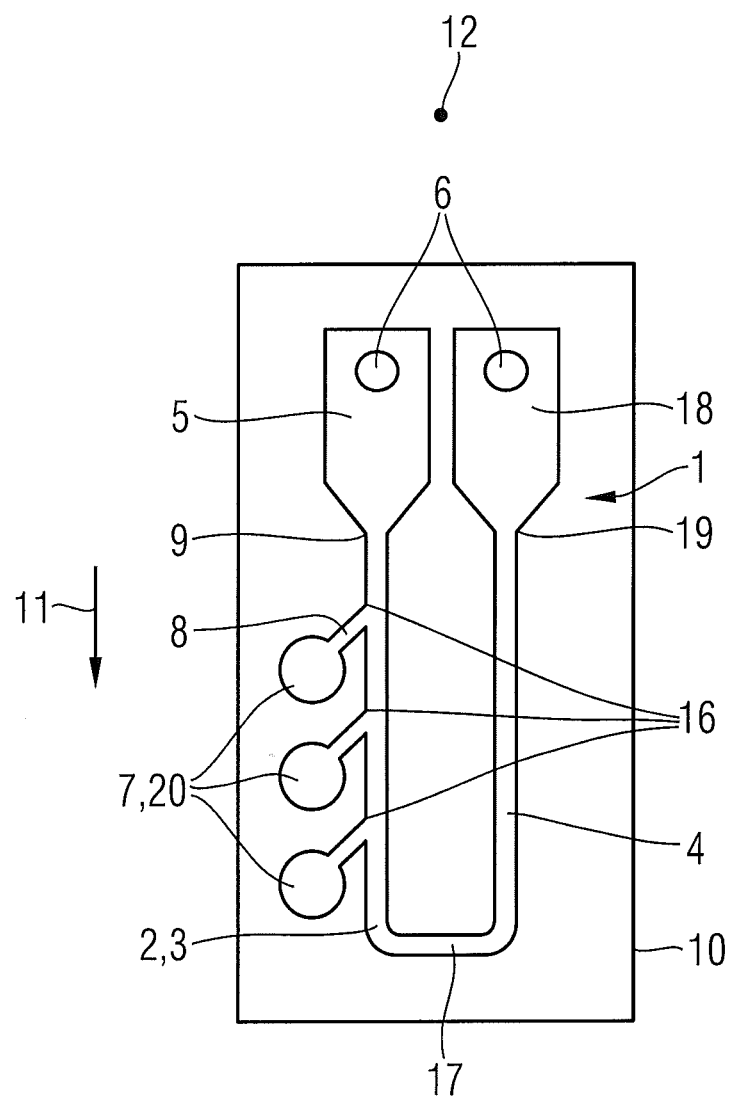
FIG. 3 depicts a schematic top view illustrating a variant of the microfluidic structure of FIG. 1.

With particular reference to FIG. 3, another exemplary embodiment of the microfluidic structure 1 for the automated analysis of liquid samples according to the invention is explained. Specifically, e.g., the structure 1 is a variant of the microfluidic structure of FIG. 1. In order to avoid unnecessary repetitions, only differences with respect to the embodiment of FIG. 1 are explained and, otherwise, reference is made to the explanations given above in connection with FIG. 1.

Accordingly, the microfluidic structure 1 in the illustrated embodiment includes an essentially U-shaped flow channel 2 comprised of two linearly extending first and second channel portions 3, 4 connected by the third channel portion 17. The first channel portion 3 is in fluid communication with plural dead-end reaction chambers 7 in which a reaction between the sample and one or more reagents can take place. First and second fluid reservoirs 5, 18 open into the first and second channel portions 3, 4, respectively, at first and second reservoir openings 9, 19. Contrary to the first and second reservoir openings 9, 19 of FIG. 1, the first and second reservoir openings 9, 19 of FIG. 3 have no inter-distance with respect to each other relative to the centrifugal force 11. In other words, the first and second reservoir openings 9, 19 have a same radial position relative to the spin axis 12.

Figure 4A:
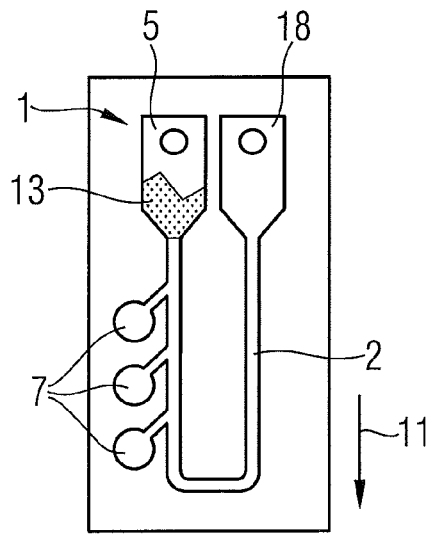
FIGS. 4A-4D depict schematic top views illustrating an exemplary embodiment of the method for the automated analysis of liquid samples using the microfluidic structure of FIG. 3.
Figure 4B:
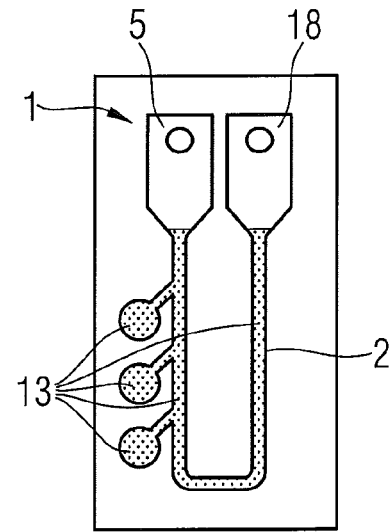
Figure 4C:
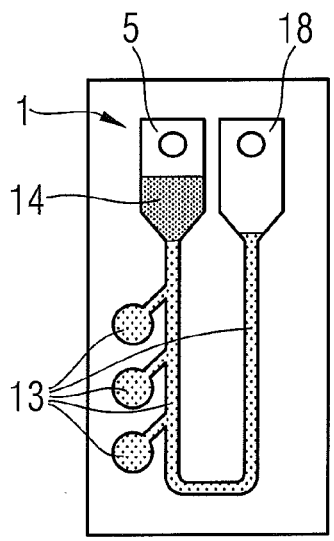

With particular reference to FIGS. 4A to 4D, an exemplary embodiment of the method of the invention using the microfluidic structure 1 of FIG. 3 is explained. Accordingly, liquid sample 13 is introduced via the port 6 into the first fluid reservoir 5 which can be performed by an automatic pipetting operation, e.g., using a pipetting robot (FIG. 4A), followed by spinning the microfluidic structure 1 around the spin axis 12 to generate centrifugal force 11 for transporting the liquid sample 13 into the flow channel 2 and the reaction chambers 7. Driven by the centrifugal force 11, the liquid sample 13 is moved until it reaches the second reservoir opening 19 of the second fluid reservoir 18. In this situation, both fluid reservoirs 5, 18 contain no liquid sample 13 (FIG. 4B).

Figure 4D:
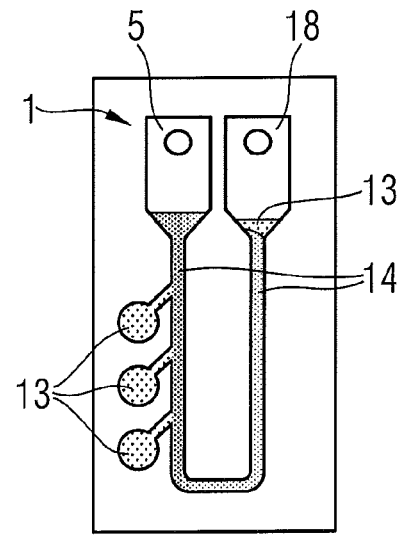

After that, control fluid 14 is introduced via the same port 6 (e.g. the left one) as used for introducing the liquid sample 13 into the first fluid reservoir 5 by an automatic pipetting operation, e.g., using a pipetting robot (FIG. 4C), followed by spinning the microfluidic structure 1 around the spin axis 12 to create centrifugal force 11 to drive the control fluid 14 into the flow channel 2 to thereby replace the liquid sample 13 contained in the flow channel 2 and to enable contact between the control fluid 14 and the sample 13 contained in the reaction chambers 7 (FIG. 4D).

The control fluid 14 then is allowed to solidify initiated by contact between the control fluid 14 and the liquid sample 13 using water as triggering agent so as to form a barrier to flow and diffusion for the liquid sample 13 contained in the reaction chambers 7.

Figure 5A:
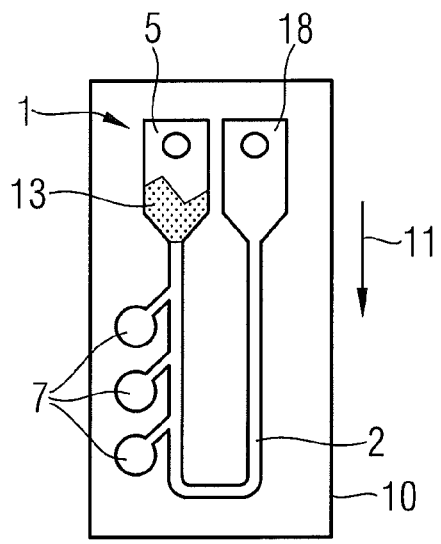
FIGS. 5A-5D depict schematic top views illustrating a variant of the method of FIGS. 4A-4D.
Figure 5B:
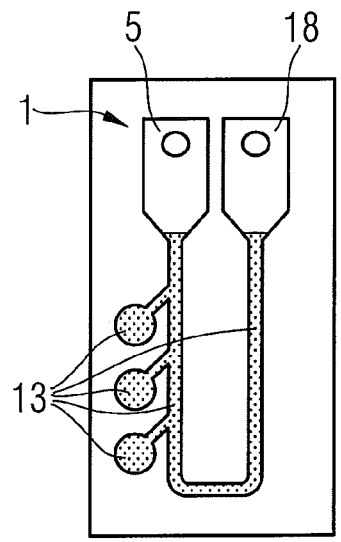
Figure 5C:
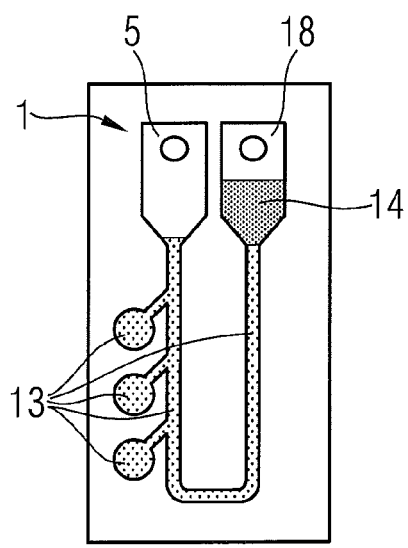

With particular reference to FIGS. 5A to 5D, a variant of the method of FIGS. 4A to 4D is explained. Accordingly, in a first step of action, liquid sample 13 is introduced via port 6 of the first fluid reservoir 5 (FIG. 5A), followed by spinning the microfluidic structure 1 around the spin axis 12 to transport the liquid sample 13 into the flow channel 2 and the reaction chambers 7 (FIG. 5B).

Figure 5D:
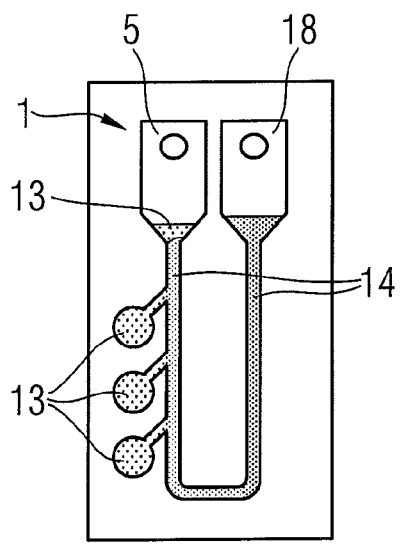

After that, control fluid 14 is introduced via the other port 6 (e.g. the right one) into the second fluid reservoir 18 (FIG. 5C), followed by spinning the microfluidic structure 1 around the spin axis 12 to drive the control fluid 14 into the flow channel 2 to thereby replace the liquid sample 13 contained in the flow channel 2 and to enable contact between the control fluid 14 and the sample 13 contained in the reaction chambers 7 (FIG. 5D).

The control fluid 14 then is allowed to solidify initiated by contact between the control fluid 14 and the liquid sample 13 using water as triggering agent so as to form a barrier to flow and diffusion for the liquid sample 13 contained in the reaction chambers 7.

Figure 6:
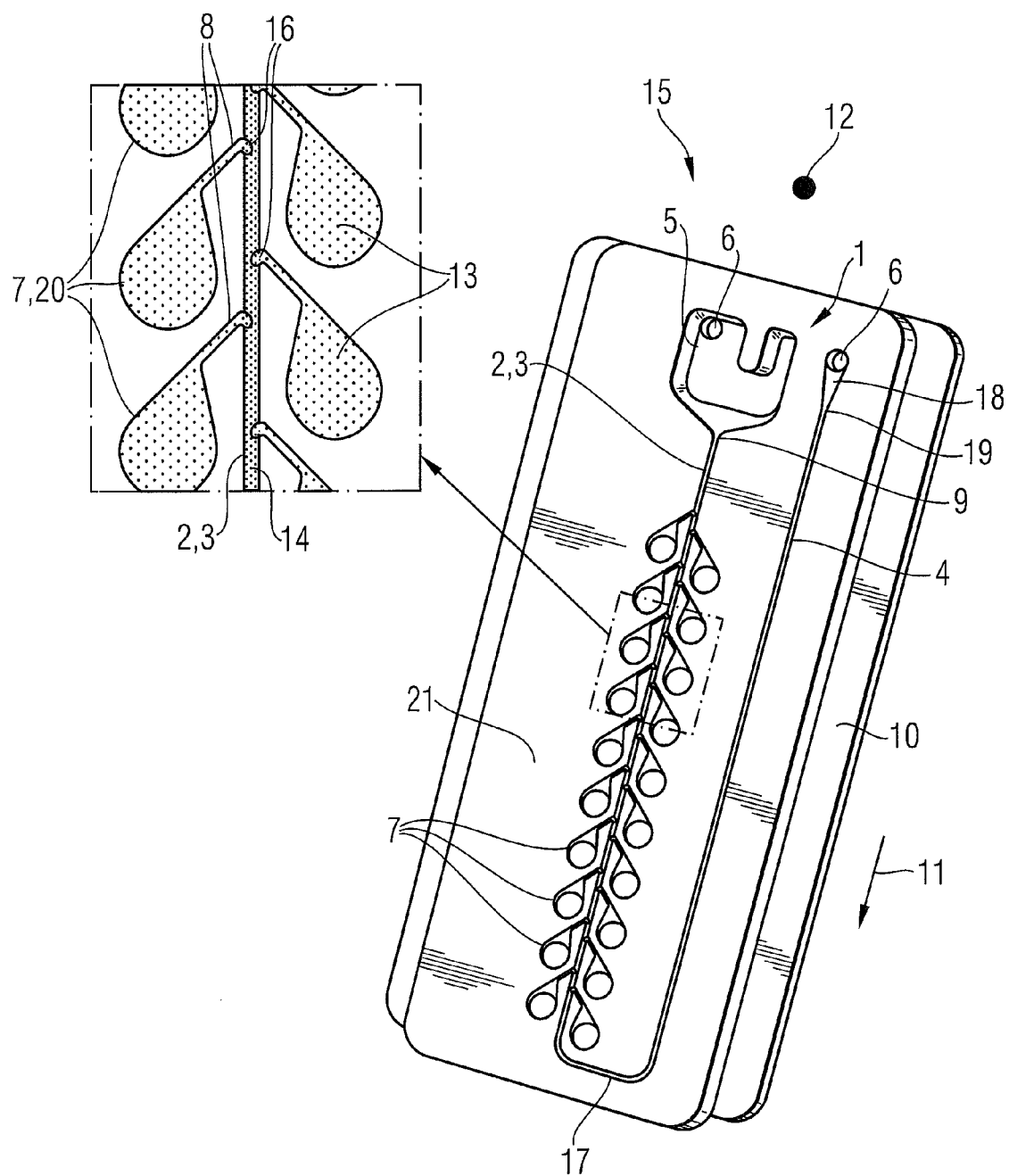
FIG. 6 depicts a perspective view of an exemplary embodiment of a microfluidic device.

Now referring to FIG. 6, an exemplary embodiment of the microfluidic device 15 of the invention is described. The microfluidic device 15 can be rotated around spin axis 12 to generate centrifugal force 11. The microfluidic device 15 includes one microfluidic structure 1 for the centrifugal force based analysis of liquid samples. The microfluidic elements of the structure 1 such as, e.g., channels, chambers, inlets, etc., are formed as recessed structure being recessed from an upper surface 21 of the solid body 10. The microfluidic elements of one microfluidic structure 1 are in fluid communication with respect to each other.

The body 10, e.g., may be made of plastic material and provided rectangular in shape. The microfluidic structure 1 may be formed by the body 10 and a cover (not illustrated). The body 10 and/or the cover may be optically transparent to enable an optical detection of a reaction product between a sample and (e.g. dry-chemical) reagent (s) which can be present in the detection chambers 7. The body 10 may also be covered by a thermally conductive sealing foil to enable thermal control of the reaction.

The body 10 may be produced by any conventional molding technique which can be used for the production of molded parts. The cover (not illustrated) may be produced by punching it from a larger piece of suitable foil. The microfluidic structure 1 can be produced by an assembly step in which the body 10 is, e.g., thermally sealed with the cover.

While only one microfluidic structure 1 is shown in FIG. 1 for the purpose of illustration only, it is to be understood that the microfluidic device 15 may be provided with plural microfluidic structures 1 according to the specific demands of the user.

Specifically, the microfluidic structure 1 of the microfluidic device 15 includes one flow channel 2 which e.g., being essentially U-shaped is comprised of first and second channel portions 3, 4 linearly extending mainly, but not necessarily, along the centrifugal force 11 generated as the microfluidic device 15 is rotated around the spin axis 12. The first and second channel portions 3, 4 are connected by a third channel portion 17 at radial-outer ends thereof, which mainly, but not necessarily, extends in orthogonal direction as to the centrifugal force 11. First and second fluid reservoirs 5, 18 open into first and second channel portions 3, 4, respectively, of the flow channel 2 by first and second reservoir openings 9, 19, respectively. Each of the first and second fluid reservoirs 5, 18 is provided with a port 6 for introducing/removing any fluid of interest into/from the fluid reservoir 5, 18. As illustrated in FIG. 6, the first and second reservoir openings 9, 19 are distanced with respect to each other relative to the direction of the centrifugal force 11.

With continued reference to FIG. 6, the first channel portion 3 is in fluid communication with plural dead-end reaction chambers 7 in which a reaction between a sample and one or more reagents can take place. The reaction chambers 7 may be arranged on both sides of the first channel portion 3 in a staggered type configuration, i.e. one reaction chamber 7 is arranged in-between two opposing reaction chambers 7. Each of the reaction chambers 7 may comprise one cavity 20 connected to one linearly extending intermediate channel 8 communicating with the flow channel 2. Otherwise, each intermediate channel 8 may branch-off from the flow channel 2 towards the reaction chamber 7 in a direction which includes a directional component in parallel alignment to the centrifugal force 11. Specifically, each intermediate channel 8 may be inclined to the centrifugal force 11 by an angle of less than about 90° so that an innermost portion of the intermediate channel 8 relative to the spin axis 12 is fluidically connected to the flow channel 2. Each intermediate channel 8 opens into the cavity 20 in an innermost portion thereof relative to the spin axis 12 to avoid undercut portions of the cavity 20 as to the direction of the centrifugal force 11. In other words, each intermediate channel 8 communicates with the cavity 20 in such a manner that the cavity 20 is in an outer position with respect to the intermediate channel 8.

With particular reference to the enlarged portion of the microfluidic device 15, the intermediate channels 8 in the illustrated embodiment tangentially open into the cavities 20. Hence, the reaction chambers 7 can be completely filled with fluid without residual air bubbles left in the cavity 20 by effect of the centrifugal force 11. As can be further taken from the enlarged detail of the microfluidic structure 1 depicted in FIG. 6, the reaction chambers 7 can be completely filled with liquid sample 13 by centrifugal force 11. Otherwise, the first channel portion 3 of the flow channel 2 can be filled with control fluid 14 while the liquid sample 13 is present in the reaction chambers 7.

Each of the reaction chambers 7 may, e.g., contain one or more pre-filled (e.g. dry-chemical) reagents for a reaction with a liquid sample. Alternatively or additionally, a reaction mixture containing a sample and one or more reagents can be driven into the reaction chambers 7.

Figure 7:
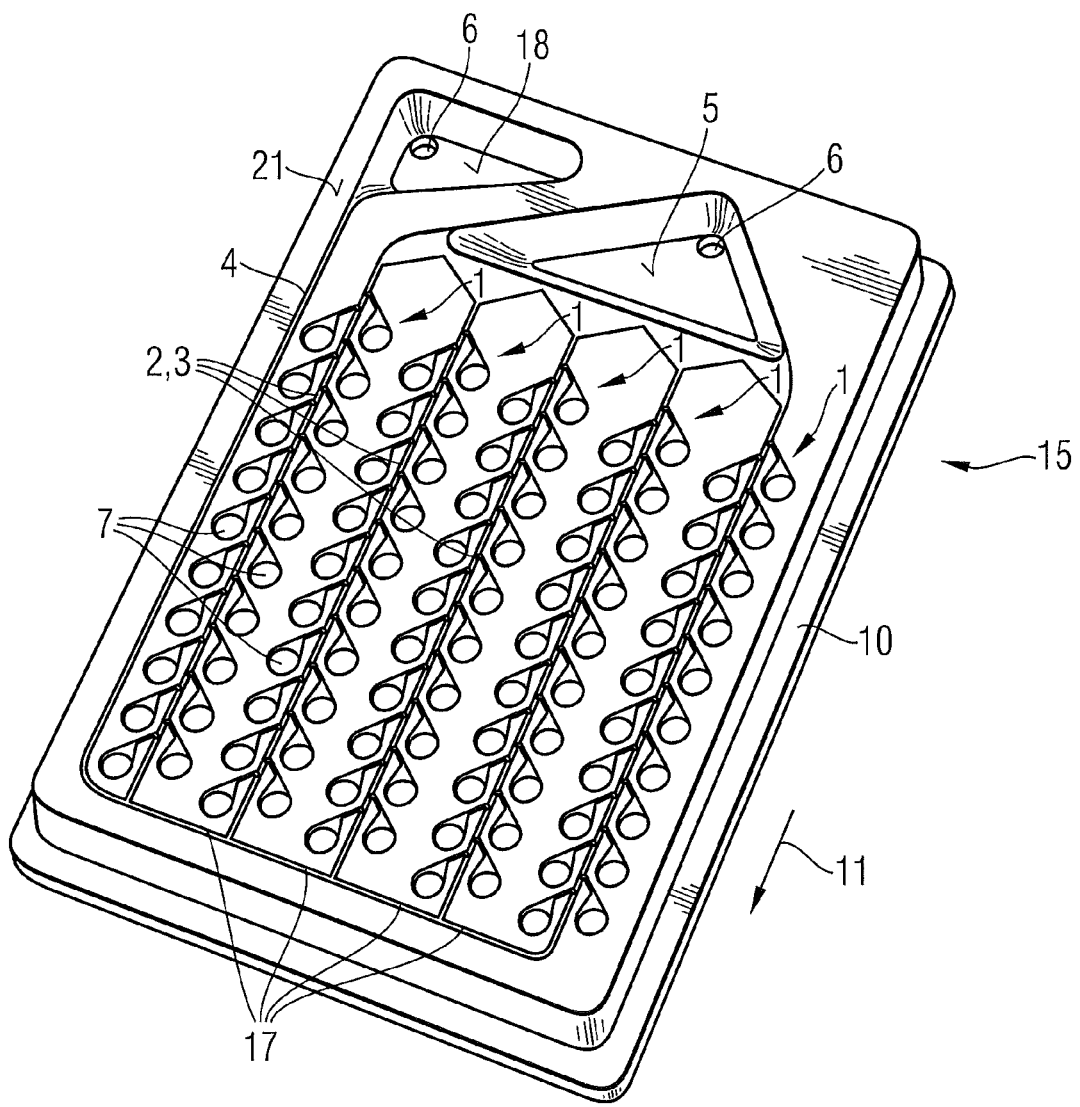
FIG. 7 depicts a perspective view of another exemplary embodiment of a microfluidic device.

Now referring to FIG. 7, another exemplary embodiment of the microfluidic device 15 of the invention is described. In order to avoid unnecessary repetitions, only differences with respect to the embodiment of FIG. 6 are described and, otherwise, reference is made to explanations given in connection with FIG. 6.

Accordingly, the microfluidic device 15 includes plural microfluidic structures 1 for automated analysis of liquid samples formed as recessed structures being recessed from an upper surface 21 of solid body 10. While a number of five microfluidic structures 1 are shown for the purpose of illustration only, it is to be understood that any other number of microfluidic structures 1 can be envisaged according to the specific demands of the user. Each microfluidic structure 1 includes a flow channel 2, which may be essentially U-shaped, is comprised of one first channel portion 3 and one second channel portion 4 linearly extending mainly, but not necessarily, along the centrifugal force 11 generated as the microfluidic device 15 is rotated around the spin axis 12. The second channel portion 4 is a common channel being part of all flow channels 2 of the microfluidic structures 1. The plural first channel portions 3 and the one second channel portion 4 are connected by one third channel portion 17 at radial-outer ends thereof, which mainly, but not necessarily, extends in orthogonal direction as to the centrifugal force 11.

The microfluidic device 15 may further include one first fluid reservoir 5 fluidically connected with and opening into all first channel portions 3 of all flow channels 2. The first fluid reservoir 5 may be provided with one port 6 for transferring any fluid of interest. The microfluidic device 15 may further include one second fluid reservoir 18 fluidically connected with and opening into the (single) second channel portion 4 of all flow channels 2. The second fluid reservoir 18 is provided with one port 6 for transferring any fluid of interest.

In the microfluidic structure and device of the present invention, each of the fluid reservoirs is designed to harbor (e.g., collect and hold) a fluid such as sample or control fluid before the fluid is moved to its final position by centrifugal force. Otherwise, the fluid reservoirs can be designed to collect liquid fluid flowing into the fluid reservoir during centrifugation. If the fluid reservoir is a chamber for sourcing fluid to be transported to the flow channel and dead-end recesses, a volume of the fluid reservoir is designed to harbor at least this volume. If the fluid reservoir is collecting fluid flowing out of the flow channel, the volume of the chamber is designed to collect this volume.

The fluid reservoirs may have a (inlet and/or outlet) port which may be designed to interface with a liquid handler or a manual liquid handling device such as a pipette. Optionally, the port may be self-closing, e.g., embodied as septum or may have closing means such as a snap or screw cover.

The fluid reservoir for sourcing or collecting may have a vent. Such vent may be a simple hole, but may also consist of a special barrier material e.g. made of hydrophobic venting material.

Thus, by the above disclosure embodiments concerning a method, structure, device, kit and system for the automated analysis of liquid samples are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A method for the automated analysis of at least one liquid sample involving the use of at least one microfluidic structure, the method comprising:

providing at least one microfluidic structure adapted for spinning around a spin axis to generate a centrifugal force wherein said at least one microfluidic structure comprises an inner position and an outer position relative to said spin axis in a direction of said centrifugal force, said at least one microfluidic structure including:
    a first fluid reservoir and a second fluid reservoir located at said inner position relative to said spin axis and only in fluid communication with each other by a U-shaped flow channel located at an outer position relative to said spin axis, said flow channel comprising a first channel portion and a second channel portion linearly extending along said direction of said centrifugal force, said first channel portion and said second channel portion connected at said outer position by a third channel portion extending in a direction orthogonal to said centrifugal force, said first fluid reservoir and said second fluid reservoir open into said first channel portion and said second channel portion respectively by a first reservoir opening and a second reservoir opening such that said first reservoir opening and said second reservoir opening have a non-zero distance with respect to each other in said direction of said centrifugal force; and one or more dead-end recesses, said one or more dead-end recesses being in fluid communication with said flow channel by one or more respective recess openings provided only in said first channel portion;
  transferring said at least one liquid sample into said first fluid reservoir;
  spinning said at least one microfluidic structure around said spin axis so as to transport said at least one liquid sample into said one or more dead-end recesses by said centrifugal force;
  transferring a control fluid into said first fluid reservoir or said second fluid reservoir;

spinning said at least one microfluidic structure around said spin axis to transport said control fluid into said flow channel by said centrifugal force so that said control fluid is at least present at said one or more respective recess openings of said one or more dead-end recesses, said control fluid generating a barrier to flow and diffusion of said at least one liquid sample contained in said one or more dead-end recesses; and analyzing said at least one liquid sample contained in said one or more dead-end recesses.

2. The method according to claim 1, wherein said at least one liquid sample and one or more reagents for reacting with said at least one liquid sample are transferred into said one or more dead-end recesses.

3. The method according to claim 2, further comprising solidifying said control fluid in at least a contact area of said at least one liquid sample and said control fluid.

4. The method according to claim 1, further comprising solidifying said control fluid in at least a contact area of said at least one liquid sample and said control fluid.

5. The method according to claim 4, wherein solidification of said control fluid is initiated by a triggering agent.

6. The method according to claim 4, wherein solidification of said control fluid is initiated by water contained in said at least one liquid sample.

7. The method according to claim 1, further comprising cycling said at least one liquid sample contained in said one or more dead-end recesses through a series of temperature excursions.

8. The method according to claim 1, wherein said one or more dead-end recesses are one or more reaction chambers and said one or more respective recess openings are one or more chamber openings.

* * * * *